United States Patent [19]

Ellison

[11] Patent Number: 4,517,965

[45] Date of Patent: May 21, 1985

[54] TISSUE RETRACTOR

[76] Inventor: Arthur E. Ellison, Adams Rd., Williamstown, Mass. 01267

[21] Appl. No.: 508,251

[22] Filed: Jun. 27, 1983

[51] Int. Cl.³ ............................................. A61B 17/02
[52] U.S. Cl. ...................................... 128/20; 128/754
[58] Field of Search ........................................ 128/4–8, 128/20, 303.1, 329 R, 749, 751–754, 642, 419 P, 785, 786

[56] References Cited

U.S. PATENT DOCUMENTS

| | | | |
|---|---|---|---|
| 1,798,124 | 3/1931 | Hunn | 128/20 |
| 2,811,971 | 11/1957 | Scott . | |
| 3,001,522 | 9/1961 | Silverman | 128/754 |
| 3,040,739 | 6/1962 | Grieshaber | 128/20 |
| 3,404,677 | 10/1968 | Springer | 128/751 |
| 3,410,269 | 11/1968 | Hourck | 128/329 |
| 3,716,058 | 2/1973 | Tanner, Jr. . | |
| 3,857,386 | 12/1974 | Ashbell | 128/20 |
| 3,929,123 | 12/1975 | Jamshidi | 128/754 |
| 3,964,468 | 6/1976 | Schulz | 128/751 |
| 4,051,844 | 10/1977 | Chiulli | 128/20 |
| 4,116,232 | 9/1978 | Rabban | 128/20 |
| 4,182,327 | 1/1980 | Haley . | |
| 4,200,111 | 4/1980 | Harris | 128/751 |
| 4,235,238 | 11/1980 | Ogiu et al. . | |
| 4,243,047 | 1/1981 | Olsen | 128/751 |
| 4,396,021 | 8/1983 | Baumgartner | 128/751 |

OTHER PUBLICATIONS

J. B. McGinty, "Arthroscopy of the Knee: Update and Review", Orthopedics Digest/Nov./Dec. 1979, pp. 17–35.

"Arthroscopic Retractor–Improves Field of Vision", Techmedica Inc., Surgical Products, Feb. 1984.

Primary Examiner—Edward M. Coven
Assistant Examiner—Max F. Hindenburg
Attorney, Agent, or Firm—Kenway & Jenney

[57] ABSTRACT

Tissue retractor particularly adapted for use during arthroscopic surgery on the knee joint. This surgical instrument includes a rigid elongate member with a sharpened end adapted for insertion through skin into meniscal tissue within the knee joint. The elongate member includes a retractable, laterally projecting barb near the sharpened end for seating within the tissue. In one embodiment, a tensioning device is provided so that parts of torn meniscal tissue can be pulled together to permit healing.

5 Claims, 6 Drawing Figures

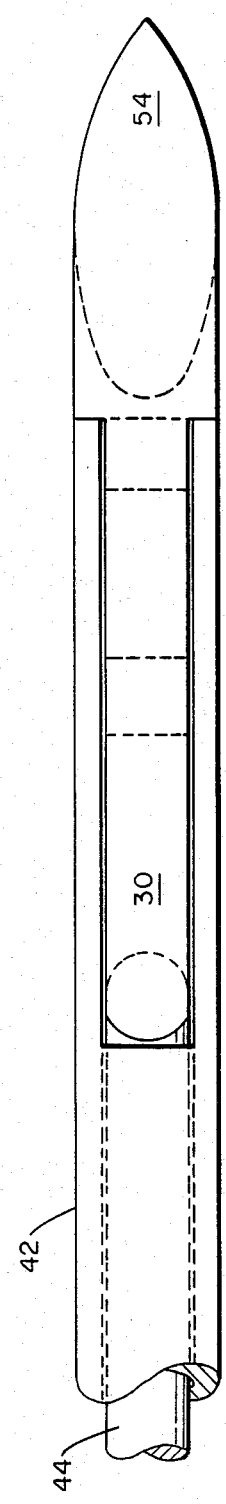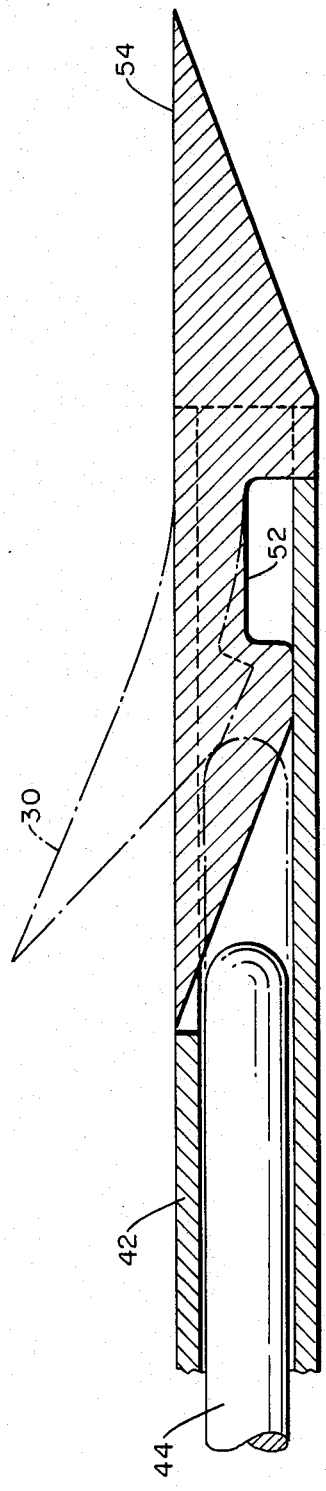

TISSUE RETRACTOR

BACKGROUND OF THE INVENTION

This invention relates to surgical apparatus and more particularly to a tissue retractor for use during arthroscopic surgery on the knee joint.

The arthroscope is a small telescope-like device which can be inserted through the skin into a knee joint permitting visualization of conditions within the knee joint. The development of the arthroscope has led to arthroscopic surgery in which only small punctures are made in the skin covering the knee joint. Arthroscopic surgery has several advantages such as rapid return to preoperative activity. The use of very small incisions is an obvious cosmetic advantage and this surgery has also resulted in low complication rates with very low incidence of infection.

Because only very small incisions are made during arthroscopic surgery, it is oftentimes difficult to grab small tags and tabs of tissue. It is generally desirable to place tissue under tension as a cut is being made so that the cut is straight and clean. Again, because of the small incisions, it is often difficult to apply the desired tension.

At the present time, there is a considerable effort devoted to repairing the meniscus arthroscopically. The meniscus is cartilege-like tissue within the knee joint. To date, however, the techniques for meniscus repair are cumbersome.

It is therefore an object of this invention to provide surgical apparatus for use during arthroscopic surgery which is able to immobilize flaps and tags of tissue and put them under tension for cutting.

It is a further object of this invention to provide apparatus which can pull torn portions of meniscal tissue together to permit healing.

Yet another object of this invention is such apparatus which is inexpensive and easy to fabricate.

Still another object of the invention is such apparatus which is readily manipulated under arthroscopic visualization within the knee joint.

SUMMARY OF THE INVENTION

The tissue retractor disclosed herein for use during arthroscopic surgery on the knee joint includes a rigid, elongate member having a sharpened end and adapted for insertion through the skin into tissue within the knee joint. The elongate member includes a retractable, laterally projecting barb near the sharpened end for seating within the tissue. When used for meniscus repair, a tensioning means is provided for placing the elongate member under tension after the barb is seated. When used as a tissue retractor, manual traction is applied so that any cutting is performed while the tissue is under tension. In a preferred embodiment, the tissue retractor includes a hollow sheath surrounding a rod which is slidingly contained within the sheath. A barb member located near an end of the sheath remains in a retracted position until the rod is moved inwardly into the sheath thereby forcing the barb to project laterally. The barb member is fabricated of spring steel so that the barb will retract flush with the sheath when the rod is withdrawn from the sheath.

BRIEF DESCRIPTION OF THE DRAWING

The invention disclosed herein will be better understood with reference to the following drawing of which:

FIGS. 5 and 6 are sectional views of the tip section of the tissue retractor shown in FIGS. 3 and 4.

DESCRIPTION OF THE PREFERRED EMBODIMENTS

Figure 1:
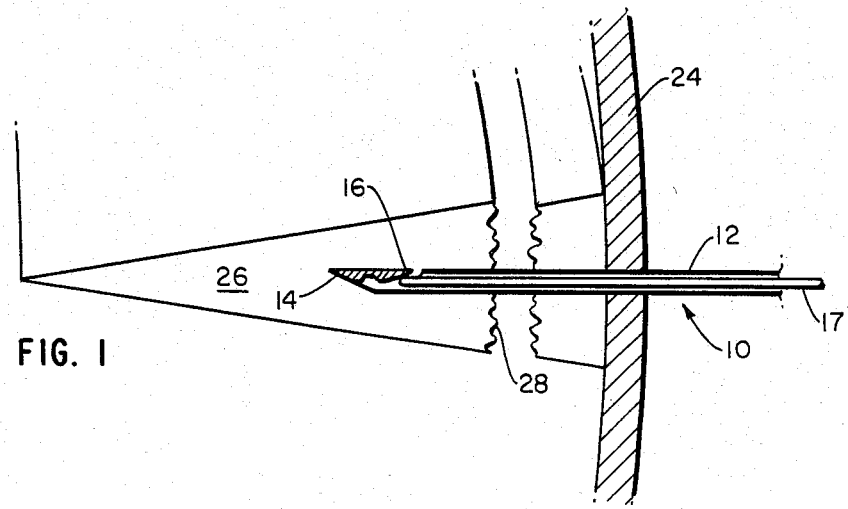
FIG. 1 is a schematic sectional view showing one embodiment of this invention being inserted into meniscal tissue.
Figure 2:
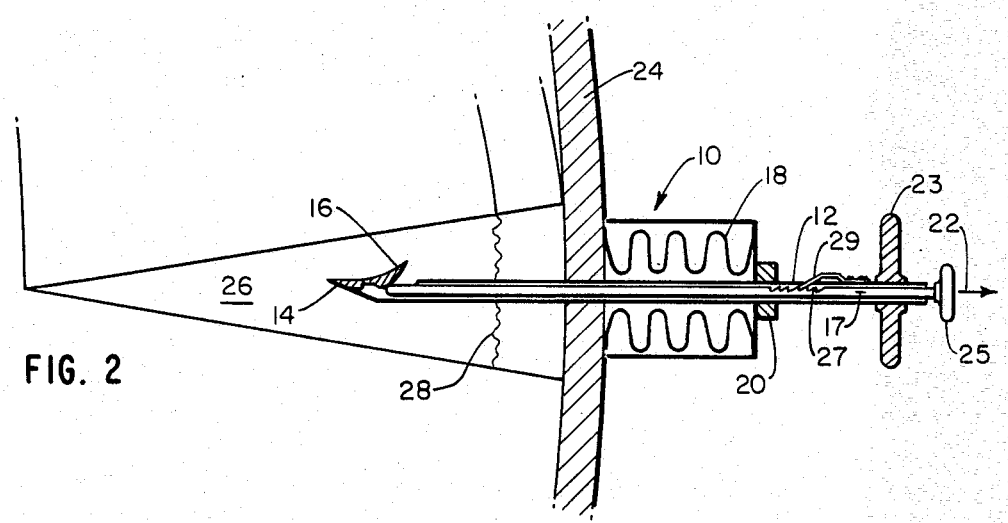
FIG. 2 is a schematic sectional view illustrating a tensioning means urging the torn portions of meniscal tissue together.
Figure 3:
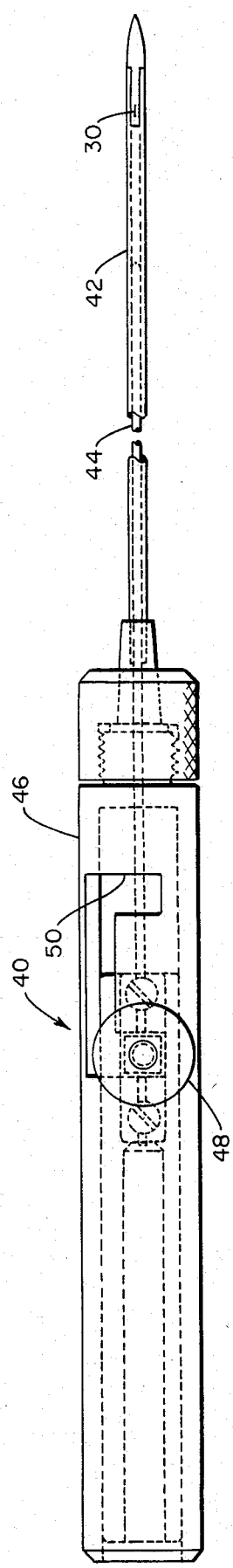
FIG. 3 is a plan view, partly in section, of a preferred embodiment of the invention disclosed herein.
Figure 4:
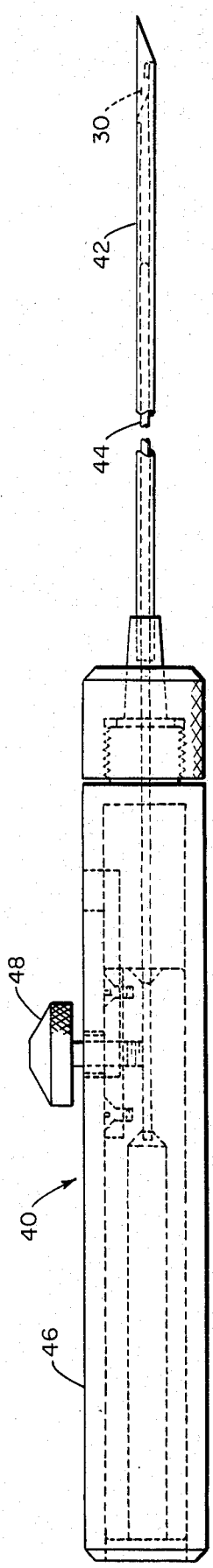
FIG. 4 is a side elevation view, partly in section, of the tissue retractor disclosed herein.

With reference first to FIGS. 1 and 2, the tissue retractor 10 includes a rigid, elongate hollow sheath 12 such as a hypodermic needle. One end 14 is sharpened and includes a retractable barb 16. A rod or obdurator 17 has a diameter so that the rod 17 will slide within the sheath 12. As the rod 17 is advanced into the sheath 12 and contacts the slanted edge of the retractable barb 16, the barb will be urged into its erect or lateral position as shown in FIG. 2. The barb 16 is made of spring steel so that it will retract flush with sheath 12 when the rod 17 is withdrawn. As shown schematically in FIG. 2, tensioning apparatus such as a spring 18 is suitably attached to the elongate member 12 at a location 20 so that the retractor 10 is urged outwardly in the direction of an arrow 22.

As shown in FIGS. 1 and 2, the tissue retractor 10 is inserted through skin 24 covering the knee joint and into meniscal tissue 26. FIGS. 1 and 2 illustrate the repair of a tear 28 in the meniscal tissue 26. To repair the tear 28, the retractor 10 is pushed through the skin 24 into the intact meniscus, across the tear 28, and into the displaced portion of the meniscal tissue 26. After the retractor 10 is seated within the displaced portion of the meniscal tissue 26, the rod 17 is advanced inwardly forcing the barb 16 into its erect position. FIG. 2 illustrates one way in which the rod 17 can be moved inwardly and locked in place. Flanges 23 are grasped and a button 25, attached to the rod 17, is pushed with the thumb to advance the rod 17 which in turn erects the barb 16. The rod 17 includes grooves 27 which cooperate with a latch 29 to create a ratchet mechanism. Thus the rod 17 will remain in the advanced position until released. The laterally extending barb 16 thus allows the portions of the meniscal tissue to be pulled together as shown in FIG. 2 when tension is applied to the elongate member 12 in the direction of the arrow 22 by means of the spring 18, for example. The tissue retractor 10 can be left in place until the tear 28 has healed. It is contemplated that a plaster cast (not shown) will cover the portion of the retractor 10 protruding outside the knee joint to protect it during the healing process. After the tear 28 has healed, the cast would be removed, the barb 16 retracted by releasing the latch 29, and the retractor 10 removed. It should also be apparent that the retractor 10 can be used to fix a loose tab or tag of tissue so that it can be cut off while under tension and then removed.

Another embodiment of the invention will now be described with reference to FIGS. 3 through 6. In this embodiment, a laterally projecting barb 30 can be erected and retracted to permit ease of removal or relocation of a tissue retractor 40. The tissue retractor 40 includes a hollow sheath 42 similar to a hypodermic needle which includes therewithin a rod 44. The rod 44 has a diameter which permits it to slide within the sheath 42. A suitable sheath has a 0.05 inch outer diameter and a 0.03 inch inner diameter. A suitable sheath length is 4 inches. The sheath 42 is attached to a handle 46 which includes a knob 48 attached to the rod 44. As can be seen more clearly in FIG. 3, the knob 48 can be moved laterally and then forwardly after which it can be locked in a slot 50. As the knob 48 is pushed forwardly, the rod 42 engages the barb 30 forcing it into its operating position as shown in FIG. 6. Thus, as the rod 44 moves to the right in FIG. 6, the barb 30, which normally rests flush within the sheath 42, is forced into the position illustrated in phantom in FIG. 6. The barb member 30 is made of spring steel so that as the rod 44 is retracted, the barb 30 will resume a retracted position substantially flush with the sheath 42. A cut out portion 52 results in a cross section suitable for the flexing of the barb 30. The barb member 30 also includes a sharpened end portion 54 allowing the apparatus 40 to be inserted easily through the skin and into the meniscus within the knee joint.

During arthroscopic surgery, the tissue retractor 40 is inserted through skin covering the knee joint and into tissue desired to be fixed. Once the retractor 40 is in the desired location, the rod 44 is advanced by means of the knob 48 and locked into the advanced position by means of the slot 50. As the rod 44 advances, the barb member 30 assumes the operative position as shown in FIG. 6 thus fixing tissue and allowing it to be put under tension for cutting or removal, or for drawing torn portions of tissue together to permit healing. If the tissue retractor 40 is not located properly, it is advanced slightly and the rod 44 retracted by means of the knob 48 thereby allowing the barb 30 to assume its retracted position. The meniscus retractor 40 can then be removed or relocated as necessary.

While the present invention has been described particularly in regard to arthroscopic surgery on the knee joint, it should be understood that the tissue retractor disclosed herein is generally suited for seating within other tissue besides meniscal tissue. It should also be recognized that a tissue retractor as disclosed herein can be made of a material which will be absorbed by the body after tissue healing. In such a case, the retractor would not have to be removed.

It is thus seen that the objects of this invention have been achieved in that there has been disclosed a tissue retractor which will seat within meniscal tissue so that it can be put under tension for cutting or for joining torn portions of tissue for healing. In the preferred embodiment, a laterally projecting barb is retractable so that the apparatus can be relocated or removed with ease.

It is recognized that variations and modifications will be apparent to those skilled in the art and it is intended that all such variations and modifications be included within the scope of the appended claims.

What is claimed is:

1. A tissue retractor for use during arthroscopic surgery on the knee joint comprising:
   a hollow sheath;
   a rod slidingly contained within said sheath; and a barb member including a slanted edge, said barb member attached to said sheath near an end of said sheath, said barb member remaining in a retracted position flush with said sheath until said rod is advanced into said sheath and engages said slanted edge thereby forcing said barb to project laterally beyond said sheath into an erect operating position, said barb member fabricated of a spring material so that it will retract flush with said sheath when said rod is retracted.

2. The tissue retractor of claim 1 wherein said barb member is fabricated of spring steel.

3. The tissue retractor of claim 1 further including a handle attached to said sheath, said handle incorporating means for fixing the axial location of said rod.

4. The tissue retractor of claim 1 further including means for placing said sheath under tension after said barb is seated within the tissue.

5. The tissue retractor of claim 4 wherein said tensioning means includes a spring attached to the end of said sheath opposite to the end near said barb member.

* * * * *